(12) United States Patent
Silver et al.

(10) Patent No.: US 7,255,681 B1
(45) Date of Patent: Aug. 14, 2007

(54) DIAPHRAGM PUMP AND PUMP FOR DOUBLE-BREAST PUMPING

(75) Inventors: Brian H. Silver, Cary, IL (US); Larry D. Annis, Elgin, IL (US)

(73) Assignee: Medela Holding AG (CH)

( * ) Notice: Subject to any disclaimer, the term of this patent is extended or adjusted under 35 U.S.C. 154(b) by 1176 days.

(21) Appl. No.: 09/591,749

(22) Filed: Jun. 12, 2000

Related U.S. Application Data

(60) Division of application No. 09/055,101, filed on Apr. 3, 1998, now Pat. No. 6,257,847, which is a continuation-in-part of application No. 08/510,714, filed on Aug. 3, 1995, now Pat. No. 5,776,098.

(51) Int. Cl.
*A61M 1/06* (2006.01)

(52) U.S. Cl. ...................................................... 604/74

(58) Field of Classification Search ............ 604/65–67, 604/73–76, 30, 31, 35–38, 118, 119, 120, 604/121; 128/DIG. 12, DIG. 13; 417/415; 251/208, 206, 209
See application file for complete search history.

(56) References Cited

U.S. PATENT DOCUMENTS

| | | | |
|---|---|---|---|
| 823,316 A | 6/1906 | Andersen |
| 1,113,942 A | 10/1914 | Anderson |
| 1,184,293 A | 5/1916 | Zeratsky |
| 1,259,309 A | 3/1918 | Somers |
| 1,460,927 A | 7/1923 | Thompson et al. |
| 1,509,226 A | 9/1924 | Brown |
| 1,596,520 A | 8/1926 | Eskholme et al. |
| 1,644,257 A | 10/1927 | Lasker |
| 2,060,063 A | 11/1936 | Frimand |
| 2,419,795 A | 4/1947 | Saunders |
| 2,542,505 A | 2/1951 | Gascoigne |
| 2,545,857 A | 3/1951 | Perkins et al. |
| 3,238,937 A | 3/1966 | Stein |
| 3,382,867 A | 5/1968 | Reaves |
| 3,782,385 A | 1/1974 | Loyd |
| 3,786,801 A | 1/1974 | Sartorius |

(Continued)

FOREIGN PATENT DOCUMENTS

CH   251810   9/1948

(Continued)

OTHER PUBLICATIONS

The Whittlestone Breastmilker, Model Havenwood MK III Operating Manual.

(Continued)

*Primary Examiner*—Manuel Mendez
(74) *Attorney, Agent, or Firm*—McDonnell Boehnen Hulbert & Berghoff LLP

(57) ABSTRACT

A motorized pump is disclosed that includes a flexible diaphragm fitting within a rigid member, a motor drive mechanism for drawing a puller member attached to the diaphragm away from the rigid member to create a space between the diaphragm and the rigid member and form a negative pressure region within that space, and an outlet communicating with the negative pressure region. In one embodiment, the pump provides a negative pressure in a single chamber which can be used to operate one or two breast shield assembles. In another embodiment, the pump is particularly adapted for double-pumping and provides two chambers which generate vacuum.

25 Claims, 14 Drawing Sheets

U.S. PATENT DOCUMENTS

| | | |
|---|---|---|
| 3,822,703 A | 7/1974 | Davisson |
| 3,931,795 A | 1/1976 | Duncan |
| 3,977,405 A | 8/1976 | Yanase |
| 3,990,816 A | 11/1976 | Kohler et al. |
| 4,200,058 A | 4/1980 | Happel |
| 4,249,481 A | 2/1981 | Adams |
| 4,263,912 A | 4/1981 | Adams |
| 4,311,141 A | 1/1982 | Diamond |
| 4,323,067 A | 4/1982 | Adams |
| 4,486,157 A | 12/1984 | Hayashi |
| 4,573,969 A | 3/1986 | Schlensog et al. |
| 4,583,970 A | 4/1986 | Kirchner |
| 4,607,596 A | 8/1986 | Whittlestone et al. |
| 4,673,388 A | 6/1987 | Schlensog et al. |
| 4,680,028 A | 7/1987 | Stuart |
| 4,710,165 A | 12/1987 | McNeil et al. |
| 4,740,196 A | 4/1988 | Powell |
| 4,759,747 A | 7/1988 | Aida et al. |
| 4,772,262 A | 9/1988 | Grant et al. |
| 4,794,915 A | 1/1989 | Larsson |
| 4,799,922 A | 1/1989 | Beer et al. |
| 4,813,932 A | 3/1989 | Hobbs |
| 4,857,051 A | 8/1989 | Larsson |
| 4,883,464 A | 11/1989 | Morifuki |
| 4,886,494 A | 12/1989 | Morifuji |
| 4,892,517 A | 1/1990 | Yuan et al. |
| 4,929,229 A | 5/1990 | Larsson |
| 4,941,433 A | 7/1990 | Hanauer |
| 4,961,726 A | 10/1990 | Richter |
| 4,964,368 A | 10/1990 | Ball et al. |
| 4,964,851 A | 10/1990 | Larsson |
| 5,007,378 A | 4/1991 | Larson |
| 5,007,899 A | 4/1991 | Larsson |
| 5,009,638 A | 4/1991 | Riedweg et al. |
| 5,049,126 A | 9/1991 | Larsson |
| 5,071,403 A | 12/1991 | Larsson |
| 5,076,769 A | 12/1991 | Shao |
| 5,178,095 A | 1/1993 | Mein |
| 5,218,924 A | 6/1993 | Thompson et al. |
| 5,295,957 A | 3/1994 | Aida et al. |
| 5,304,129 A | 4/1994 | Forgach |
| 5,308,321 A | 5/1994 | Castro |
| 5,352,096 A | 10/1994 | Chi-Wen |
| 5,358,476 A | 10/1994 | Wilson |
| 5,514,166 A | 5/1996 | Silver et al. |
| 5,571,084 A | 11/1996 | Palmer |
| 5,586,518 A | 12/1996 | Carrano |
| 5,601,531 A | 2/1997 | Silver |
| 5,616,125 A | 4/1997 | Jelks |
| 5,648,606 A | 7/1997 | Spalding |
| 5,649,809 A | 7/1997 | Stapelfeldt |
| 5,720,722 A | 2/1998 | Lockridge |
| 5,776,098 A | 7/1998 | Silver et al. |

FOREIGN PATENT DOCUMENTS

| | | |
|---|---|---|
| CH | 270694 | 12/1950 |
| DE | AS 1 203 971 | 12/1966 |
| DE | OS 1 810 549 | 7/1969 |
| DE | GM 1 851 303 | 6/1970 |
| DE | 26 58 322 | 6/1978 |
| DE | 30 05 837 A1 | 9/1980 |
| DE | 33 28 725 A1 | 2/1984 |
| DE | 162358 | 11/1985 |
| DE | 87 14995 | 2/1988 |
| DE | 41 05 097 A1 | 8/1991 |
| DE | 10 18 202 C2 | 10/1993 |
| DE | GM 295 00 740 | 4/1995 |
| EP | 0 123 269 A3 | 4/1984 |
| EP | 0 162 358 | 11/1985 |
| EP | 0 733 376 A2 | 9/1996 |
| GB | 185521 | 9/1922 |
| GB | 271857 | 10/1927 |
| GB | 660283 | 11/1951 |
| GB | 0762701 | 12/1956 |
| GB | 2 082 920 | 3/1982 |
| GB | 2 127 293 A | 4/1984 |
| IT | 407293 | 9/1944 |
| SE | 158 976 | 5/1957 |

OTHER PUBLICATIONS

*Breastfeeding A Guide For the Medical Profession*, Ruth A. Lawrence, M.D., pp. 467-469, Apr. 16, 1986.
Medela Hospital Catalogue, Medela.
Cicle Caring Brochure, Ameda Egnell.
*Nursing Know-How*, Dana Sullivan.
*Breastfeeding: Making an Informed Decision*, Kristy Gibson, GFW, May 1997.
"What's New/Best Seller", Medela Article, Bacon's May 1997.
"Mom Sings Praises of Mother's Milk", Bacon's, Jan. 1997.
"Breastfeeding Make Easier", Great Expectations, Winter, 1996.
*MEDAP*, Milchsauger P 6010.

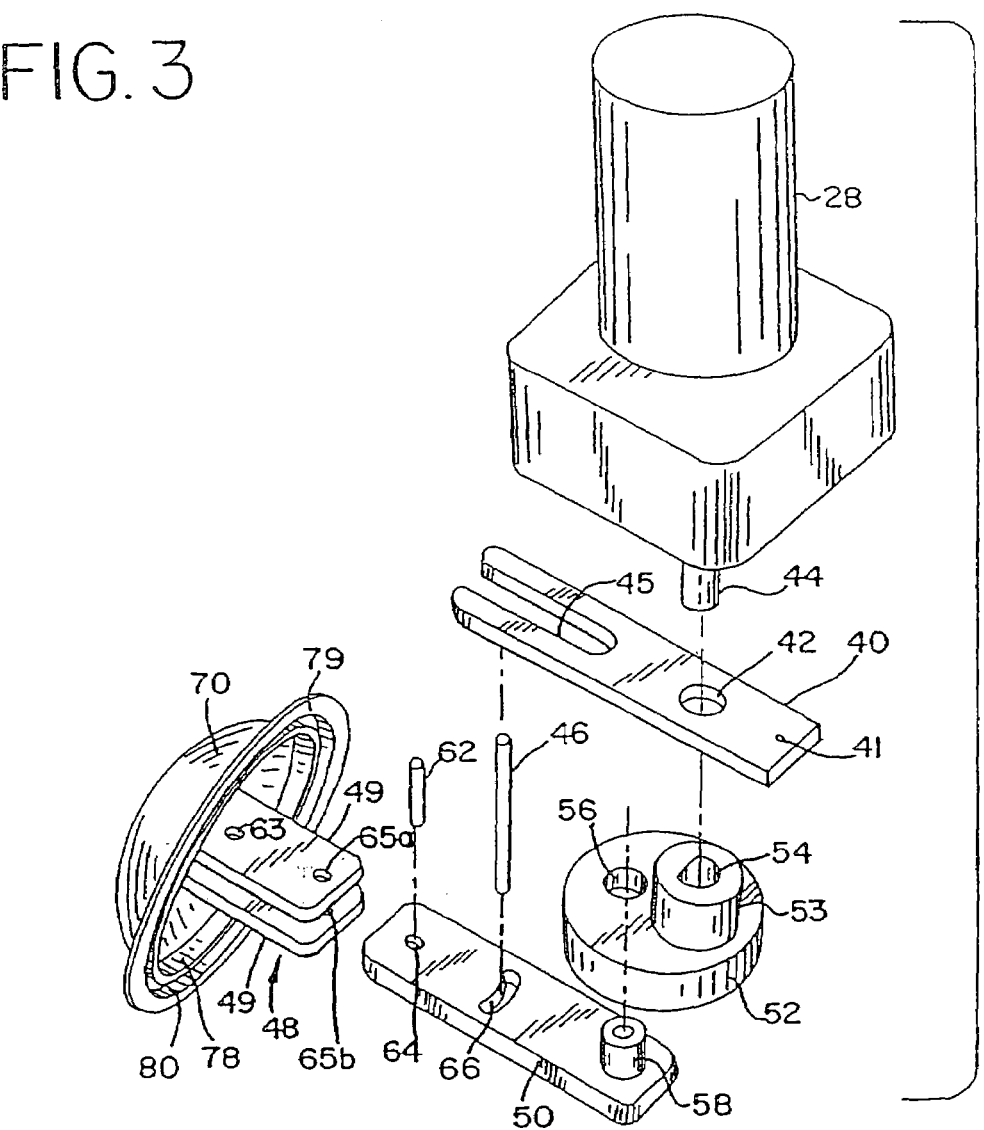

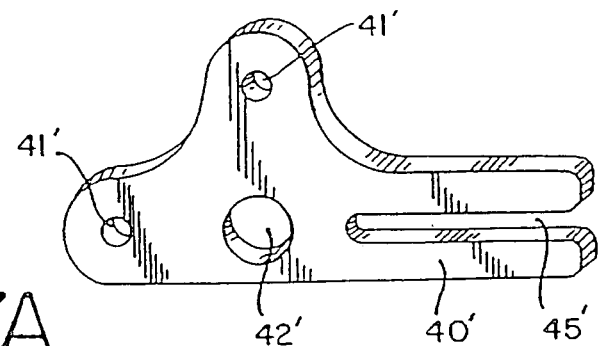
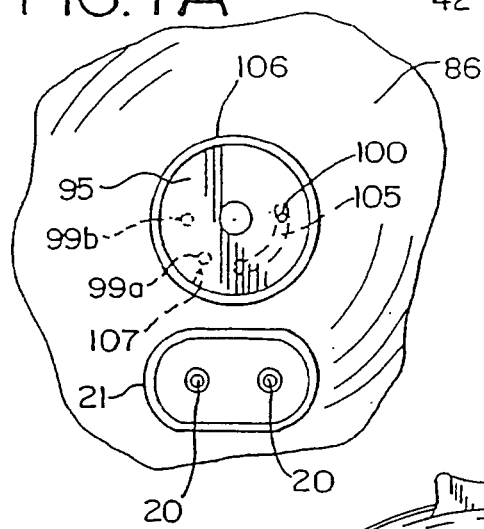
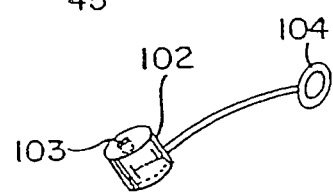
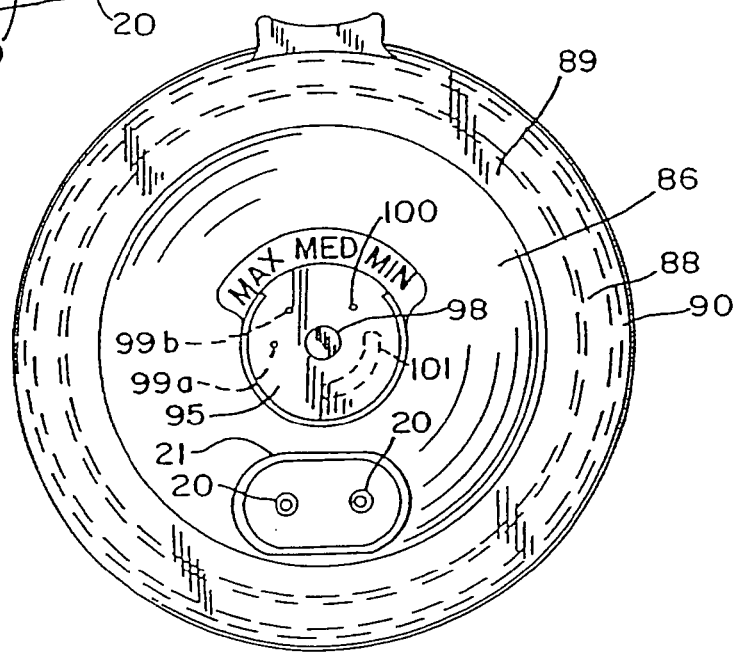

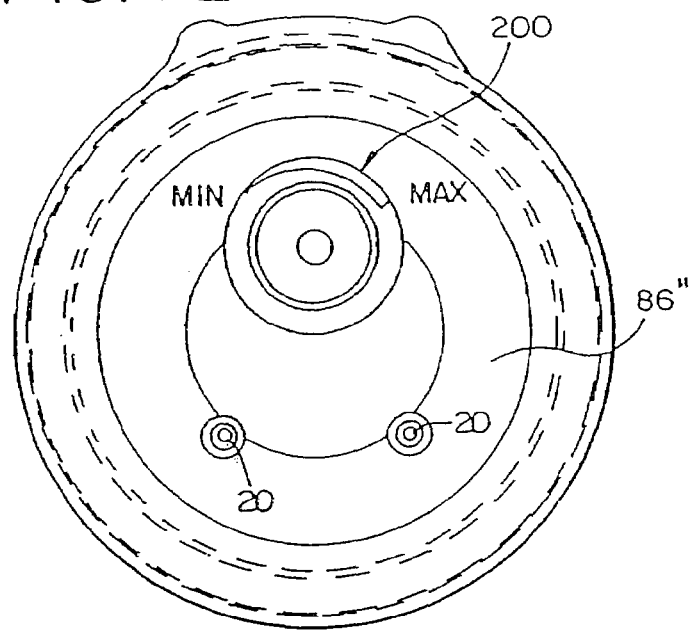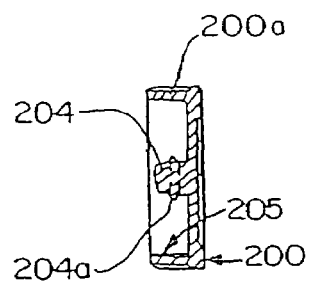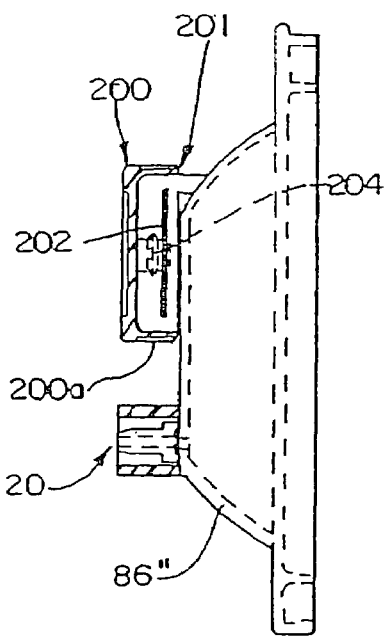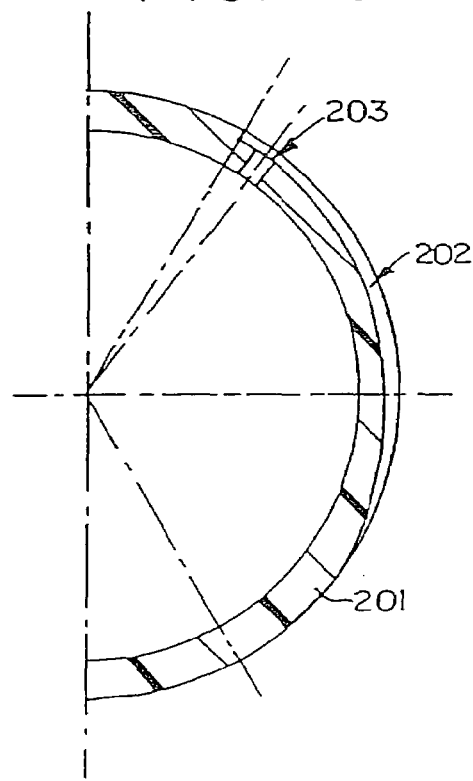

FIG. 11
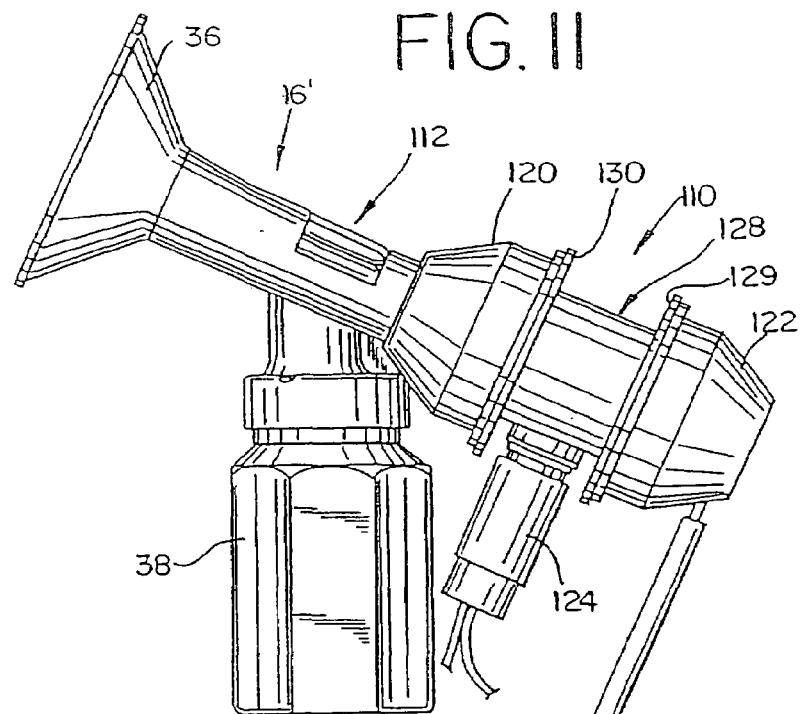
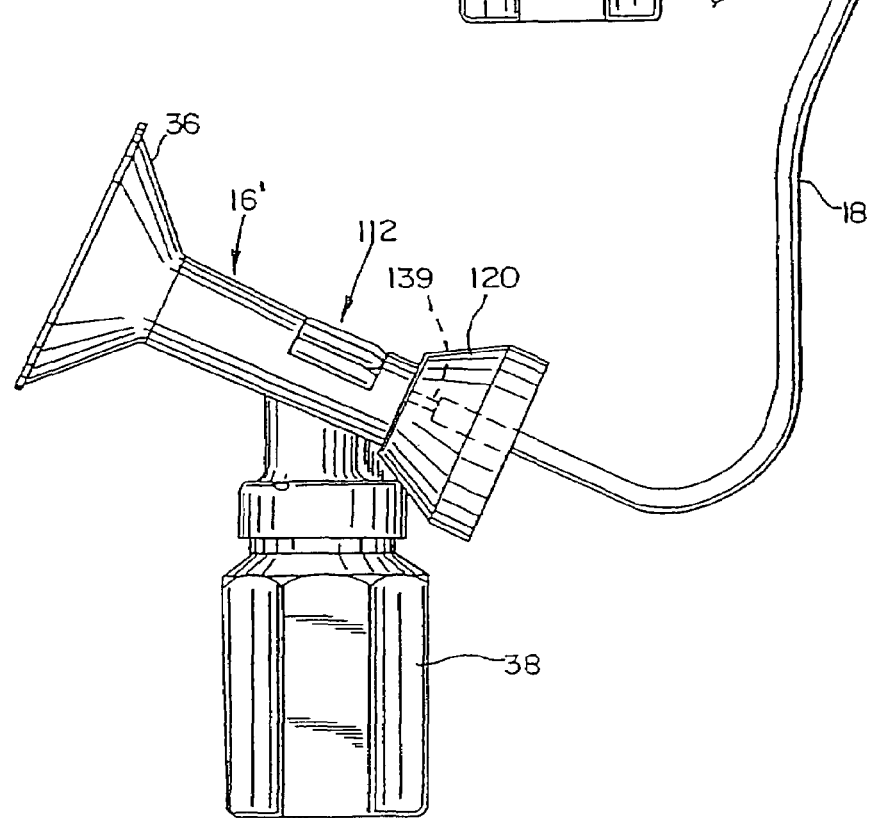

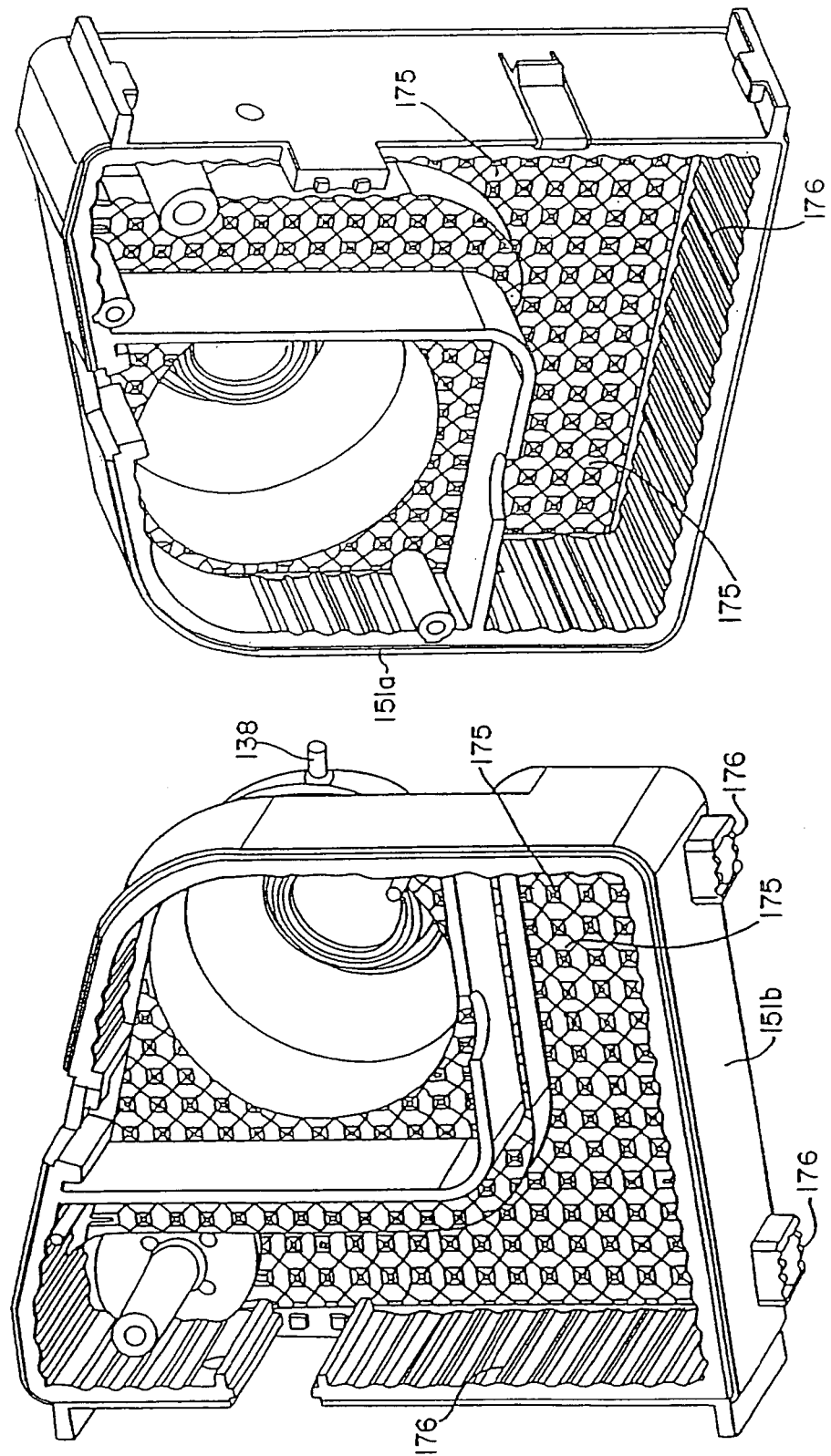

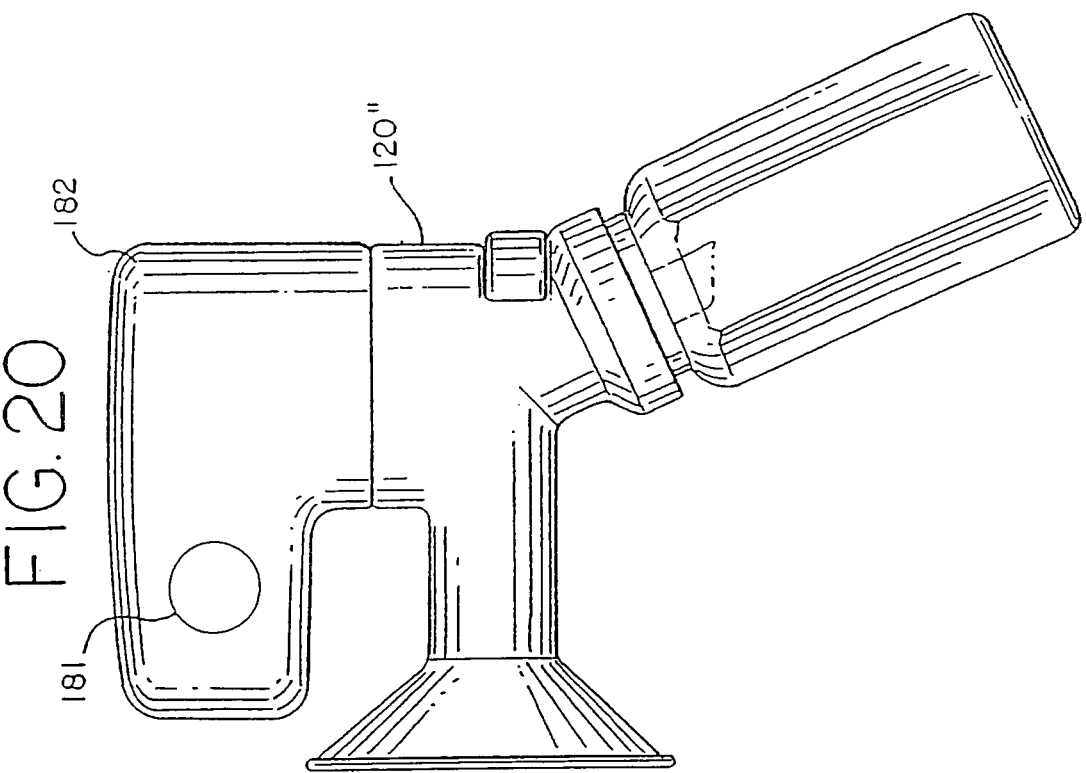
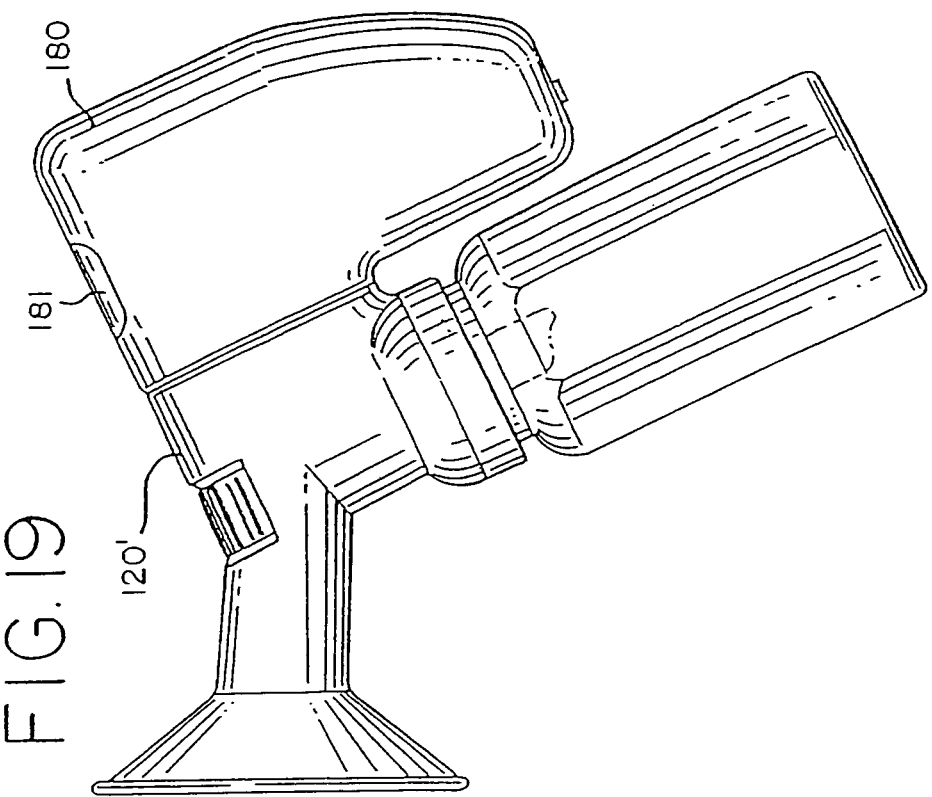

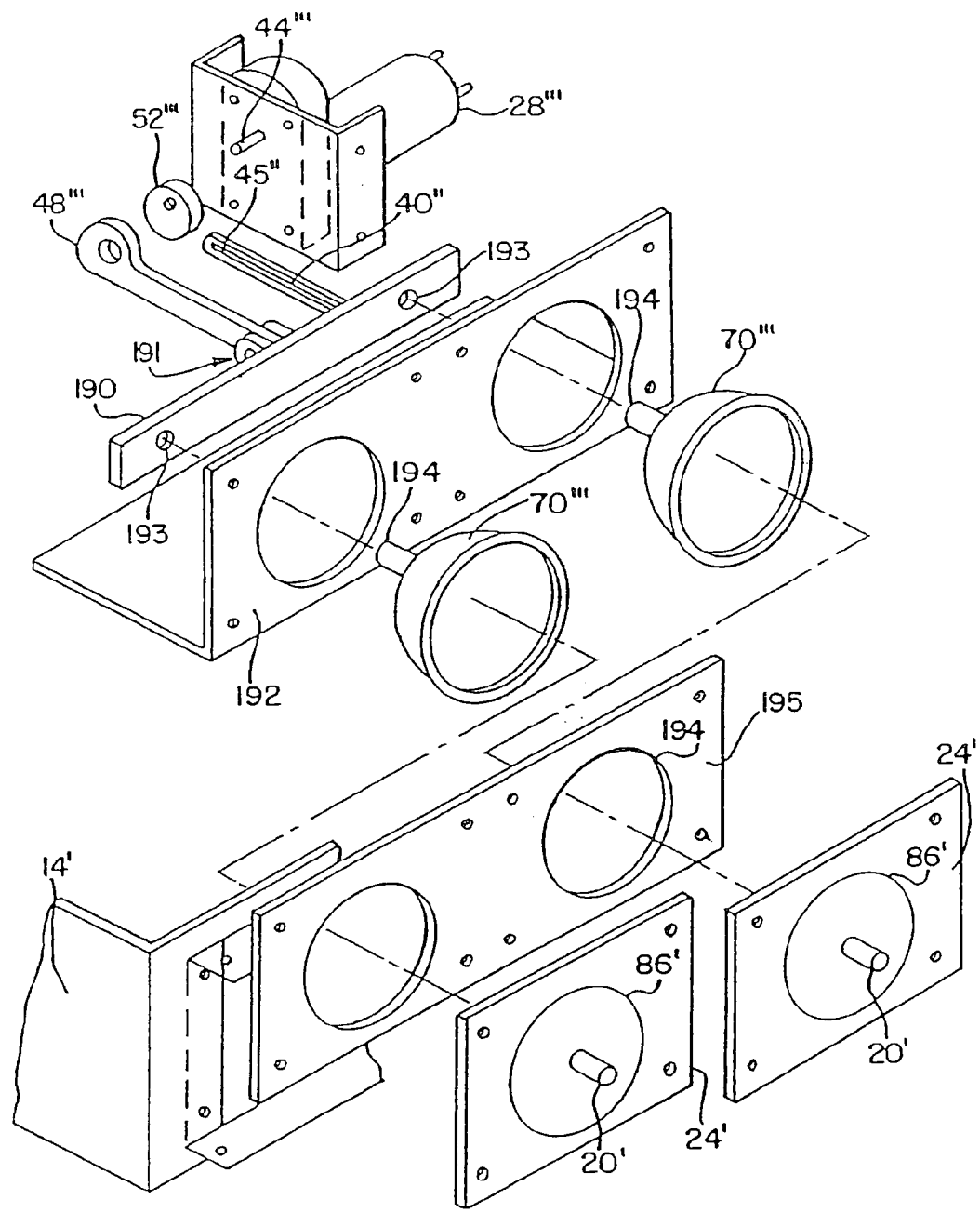

DIAPHRAGM PUMP AND PUMP FOR DOUBLE-BREAST PUMPING

RELATED PATENT APPLICATIONS

This application is a divisional of Ser No. 09/055,101 filed Apr. 3, 1998, now U.S. Pat. No. 6,257,847, which is a continuation-in-part of U.S. patent Ser. No. 08/510,714 filed Aug. 3, 1995, now U.S. Pat. No. 5,776,098.

BACKGROUND OF THE INVENTION

The invention relates to motorized pumps, and more particularly, to breastpumps.

Breastpumps are convenient for nursing mothers, because, among other things, they allow the nursing mother to draw off breast milk to feed to the child at a later time when the mother may not be present. For some mothers, breastpumps are required, particularly when the child has suckling difficulties, or if the mother has problems with excessive or deficient milk production, or cannot empty completely. Some mothers also require breastpumps in the event of soreness or injury of the mammilla, or sunken mammilla.

Manually-driven breastpumps are commonplace. However, they typically require the use of both hands to pump a single breast—one to hold the breast shield/pump in place, and the other to drive the pump. There are also manually driven breastpumps that can be operated with one hand, as by using a lever-type drive mechanism. They also obviously require some manual effort to operate.

Motor-driven pumps for breastpumps, such as battery-powered or house-current powered, also have been marketed. While eliminating the need for manually reciprocating the pumping mechanism, those pumps made for operating two breast shield assemblies at once—double-pumping—have typically been quite large, and often quite heavy. Smaller battery-powered pumps which are part of the breast shield assembly itself have not historically been adapted to, or capable of, double-pumping off the same pump.

SUMMARY OF THE INVENTION

The present invention was designed with many of the foregoing considerations in mind. It has a principal objective to provide a relatively inexpensive but efficient pump that is readily portable because it is compact and lightweight.

The motor drive mechanism of the pump has a durable drive train, and the main vacuum-generating pump components—flexible diaphragm and rigid cap—are each preferably detachably mounted together within a frame. Assembly, and disassembly—as for repair or cleaning—are therefore efficiently and easily accomplished. A pressure regulator valve mechanism on the rigid cap further provides simple manual control for varying negative pressure developed by the pump.

These features make the inventive pump ideally suited for a breastpump. More particularly, the present invention in one form is an electrically-powered diaphragm pump mounted within a support frame contained in a soft carrying case. A zippered flap in the carrying case provides access to the front of the pump unit, which has spigots for attaching tubing that connects to breast shield assemblies.

The diaphragm pump in one form of the invention has a durable drive chain comprising a drive shaft fit with an eccentric cam, to which is attached a follower. The follower is in turn pivotably connected to a puller that is attached to a flexible diaphragm. The diaphragm rests near or against the interior surface of a rigid cap, the latter being stationarily mounted. An expansible chamber is thus provided. In operation, the rotation of the drive shaft rotates the cam, causing the follower to move back and forth as it orbits the shaft. The puller moves with the follower, drawing the diaphragm away from the cap and forming a negative pressure that is communicated by one or two spigots to tubing attached to the breast shield assemblies.

It is also contemplated that the foregoing drive mechanism be adapted to drive two diaphragms in respective cap assemblies. In one such an embodiment, the puller would take the form of a yoke to which the diaphragms are connected. The follower would then reciprocate to move the puller and associated diaphragms toward and away from the caps. In another such embodiment, a pair of opposed pullers would be used in a push-pull arrangement, whereby the two pumps cycle oppositely. Of course, this diaphragm and cap assembly is but one type of expansible chamber pump that could be advantageously used with other aspects of the invention.

The pump further can include a vacuum regulator device on the cap. The regulator device can also be located elsewhere, such as anywhere between the breast shield and the vacuum source, or on the breast shield itself. In one embodiment, the vacuum regulator comprises a rotary valve member mounted for rotational movement on the rigid cap. An aperture is formed through the valve member. At least one hole or recess is formed through the cap member, and communicates with the pressure region generated between the cap interior and the diaphragm.

The valve member has a first position wherein the valve aperture and the cap hole are aligned to place the pressure region in communication with atmosphere, and a covered position wherein the valve aperture and the cap hole are unaligned, with the valve member thereby closing the cap hole. A maximum and minimum vacuum level are thereby provided, depending on whether air can be drawn within the cap or not, as controlled by the valve.

A second hole different in size from the first cap hole can be additionally provided, establishing a second position wherein the valve aperture and the second cap hole are aligned for a different vacuum level. Maximum, medium and minimum vacuum levels can thus be made available through adjustment of the cap hole sizes.

The foregoing vacuum regulator device has further been modified in another embodiment. In the latter form, the rotary valve member has a crescent-shaped channel formed in its base (the part that is in contact with the cap). The aperture through the valve member extends into this channel. Two cap holes are formed in the cap. In the minimum vacuum position, the channel overlies both cap holes; in the medium position, only one hole, and in the maximum vacuum position, neither cap hole is in communication with the channel.

In yet another embodiment, the vacuum regulator device takes the form of a ring element which is rotatably mounted on each of a pair of caps in a pump adapted for double breast pumping. The rotatable element is easily manipulated. This also enables independent control of the vacuum being generated in each breast shield assembly, for maximum convenience of the mother. The previously noted vacuum regulator devices above can likewise be used on each of the pump caps for the same advantageous independent control. Also, a continuously variable vacuum regulator device has been developed and can be used.

In a further evolution and adaptation of the foregoing invention utilizing a diaphragm pump, an apparatus has been developed which is particularly adapted for double breast pumping (although, and as will be seen, single breast pumping is also plainly included within its ambit).

In a first form of this adaptation, a double-diaphragm pumping mechanism has a pair of opposed pressure-generating units, in particular for generating a negative (vacuum) pressure. In a presently contemplated embodiment, one unit is adapted for direct attachment to a breast shield assembly. This unit has a diaphragm mechanism which is inserted into a receptacle, or collar, formed as part of the breast shield assembly. With the collar, the diaphragm forms a chamber within which a vacuum is generated. The other unit in this embodiment is self-contained, i.e., it has a diaphragm mechanism located within a rigid cover to form another (second) chamber within which a vacuum is generated. An outlet port is provided for communicating the vacuum this second chamber is generating. That outlet port is connected by tubing to another breast shield assembly.

A common drive mechanism serves to operate both of the pressure chambers of this double-diaphragm pump. In the foregoing embodiment, the drive mechanism uses an offset push-pull arrangement to create alternating negative pressure in the respective chambers. This results in alternating suction on the breasts. The double-diaphragm pumping mechanism of this embodiment (which is mounted to a breast shield assembly) is compact and light enough to be readily supported on a single hand-held breast shield assembly, such that it can be held in place by the mother on one breast with one hand, while the other breast shield assembly, which is being run off of the same pump, is held in place with the other hand.

In another form of this adaptation, the double-diaphragm pumping mechanism again has a pair of opposed pressure chambers, except they are built into a small lightweight housing, such as might be set upon a table rather than held in the hand. This pumping mechanism utilizes a pair of opposed pressure chambers and a push-pull drive arrangement to alternately create a negative pressure in a respective chamber. An outlet is provided for each chamber which is connected via tubing to a respective breast shield assembly.

In a presently contemplated embodiment, the foregoing pumping mechanism further includes a speed regulator device for controlling the rate of pumping (i.e., the suction cycle or timing between negative pressure events). The "table-top" version also has a sound-deadening construction molded into the housing.

Other features and advantages of the present invention will become apparent from the detailed description that follows taken in conjunction with the drawings, described below.

BRIEF DESCRIPTION OF THE DRAWINGS

FIG. 3 is an exploded perspective view of most of the elements of the diaphragm pump;

FIG. 4 is a perspective view of a follower;

FIG. 5 is a cross-sectional view along line 5-5 of FIG. 4;

FIG. 6 is a perspective view of an alternative embodiment of a guide for the diaphragm pump;

FIG. 7 is a front view of the diaphragm pump cap of the first embodiment;

FIG. 7A is a modified form of a vacuum regulator;

FIG. 7B is a front view of another embodiment of a vacuum regulation device;

FIG. 7C is an enlarged view of the rim upon which a disk valve rotates in the embodiment of FIG. 7B;

FIG. 7D is a disk valve for use with the rim of FIG. 7C;

FIG. 7E is a side view partly in section of the embodiment of FIG. 7B;

FIG. 10 is a perspective view of a cap for use with the pump spigots.

FIG. 11 is another embodiment of the invention in the form of a pump for double breastpumping;

FIG. 17 is a perspective view of the interior of the half of the pump casing facing away from the viewer in FIG. 16;

FIG. 18 is a perspective view of the other half of the pump casing of FIG. 16;

FIG. 19 is a side view of another design for an embodiment of the invention;

FIG. 20 is a side view of yet another design for an embodiment of the invention; and FIG. 21 is a perspective view of still another embodiment for a pump for double breast pumping.

DETAILED DESCRIPTION OF PREFERRED EMBODIMENTS

A diaphragm pump of the present invention is shown in embodiments as a vacuum (i.e., negative pressure) source for a breastpump. The diaphragm pump has uses in other environments and applications, however.

Figure 1:
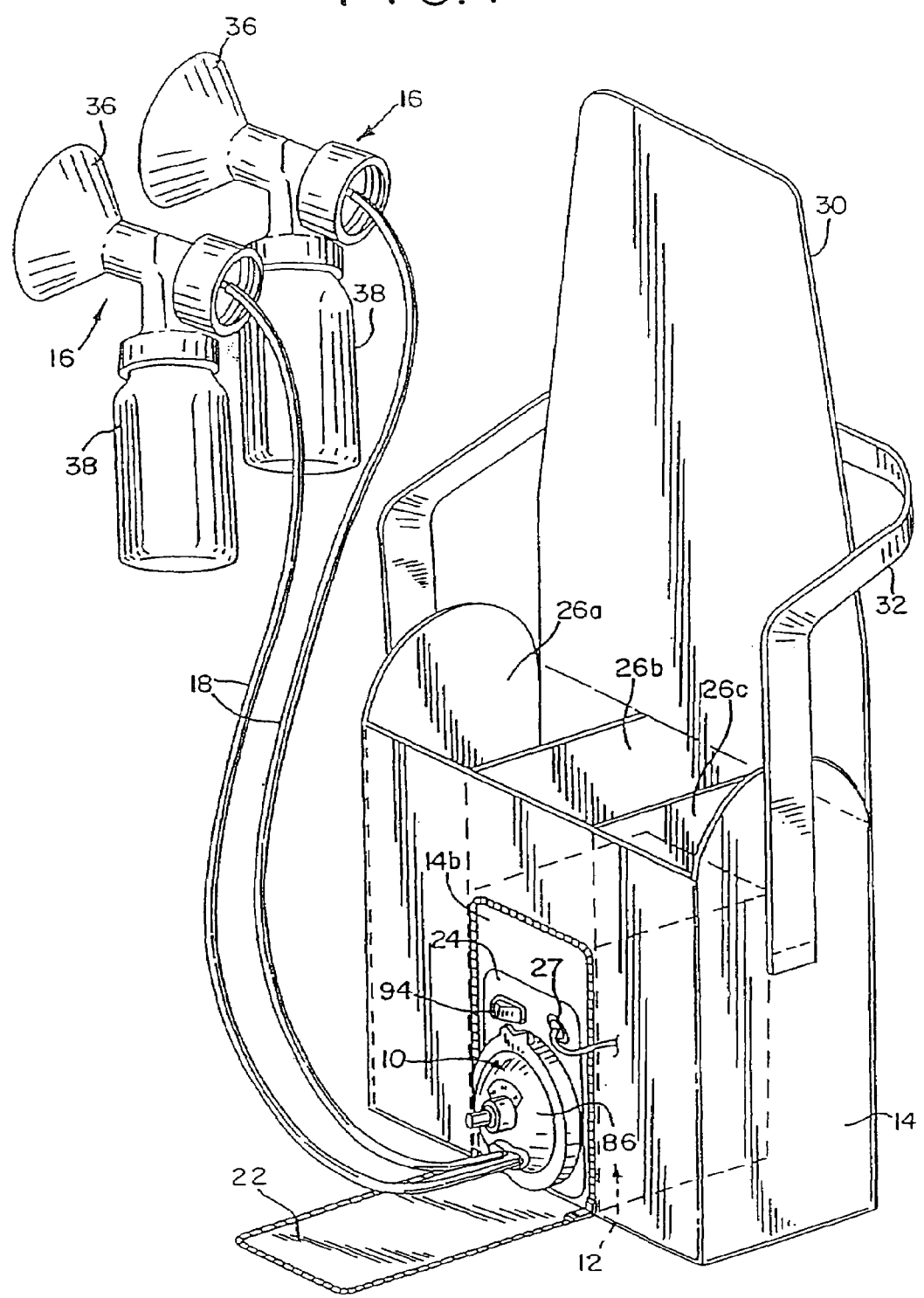
FIG. 1 is a perspective view of a first embodiment of a diaphragm pump-driven breastpump made in accordance with the present invention.

Referring to FIG. 1, a first embodiment of a diaphragm pump 10 according to the present invention is mounted within a rigid support frame 12. The support frame 12, which is somewhat boxlike, is carried and mounted within a soft carrying case or bag 14. It is shown connected to two breast shield assemblies 16 via tubing 18. Tubing 18 is attached at one end to respective spigots 20 (FIG. 2) via a slip-on fit over the spigots 20. With the tubing 18 removed from the spigots 20, the diaphragm pump 10 can be closed up within the case 14 via a zippered flap 22. Front plate 24 of the pump 10 may preferably be set back from the sidewall of the case 14 so that the zippered flap 22 is co-planar with the case front sidewall 14a when shut, although it need not be so inset. A wall 21 is formed surrounding the spigots 20 to protect the spigots from being accidentally broken off.

Case 14 has a number of interior compartments 26a, 26b, 26c, which constitute storage areas, such as for the breast shield assemblies 16, tubing 18, diapers, etc. Case 14 also could include a power source in the form of a battery (not shown) to which a commonly obtainable 12V DC gear motor 28 (FIG. 2) is electrically connected. An alternative power source could be an A.C. source (e.g., common 120 VAC service) through a DC converter, as at jack 27 (FIG. 1). The motor, power source and their various electrical connections are all conventional, and well known to those skilled in the art.

Case 14 has a flap-type closure 30, with a shoulder strap 32. Pump support frame 12 is fixed within a fabric compartment formed within the case 14. This may be by attachment of the front plate 24 to surrounding fabric 14b in a conventional manner, such as by riveting, stitching, adhering or some other common attachment. Here, front plate 24 frames the fabric 14b and captures it between the back of the plate 24 and the front 12a of the support frame 12. This is accomplished using toothed plastic rivets 34, or alternatively keyhole-type fasteners, which extend through the front plate 24, holes in the intervening fabric 14b, and then through holes provided in the front 12a of support frame 12.

The breast shield assemblies 16 are of the type sold by Medela, Inc. under the name MANUALECTRIC, and generally shown in U.S. Pat. Nos. 4,857,051 and 4,929,229, for example. The assemblies 16 have a breast shield 36 associated with a milk bottle 38. A periodic vacuum generated by the pump 10 within the shield 16 serves to extract milk, which is then collected in the bottle 38.

Pump 10 has a guide 40 (FIG. 3) fixedly mounted to an inner frame wall 12b (FIG. 2), as by machine screws (not shown) with hole 41 provided to this end. An opening 42 is made in the guide 40 through which drive shaft 44 of the motor 28 extends. The diameter of the opening 42 is wider than the drive shaft 44 so that the latter freely rotates. Guide 40 has an elongated slot 45 formed therein which serves to confine and direct the movement of a guide pin 46 extending from a puller 48 connected to a follower 50 in a manner to be described hereafter.

FIG. 6 illustrates an alternative embodiment for the guide. Guide 40' functions in the same manner as guide 40. It is mounted to the inner frame wall 12b (FIG. 2) using machine screws through holes 41', and has an elongated slot 45' for the guide pin 46. Drive shaft 44 extends through hole 42'. Prime numbers used herein describe generally similar elements to their unprimed counterparts.

Figure 2:
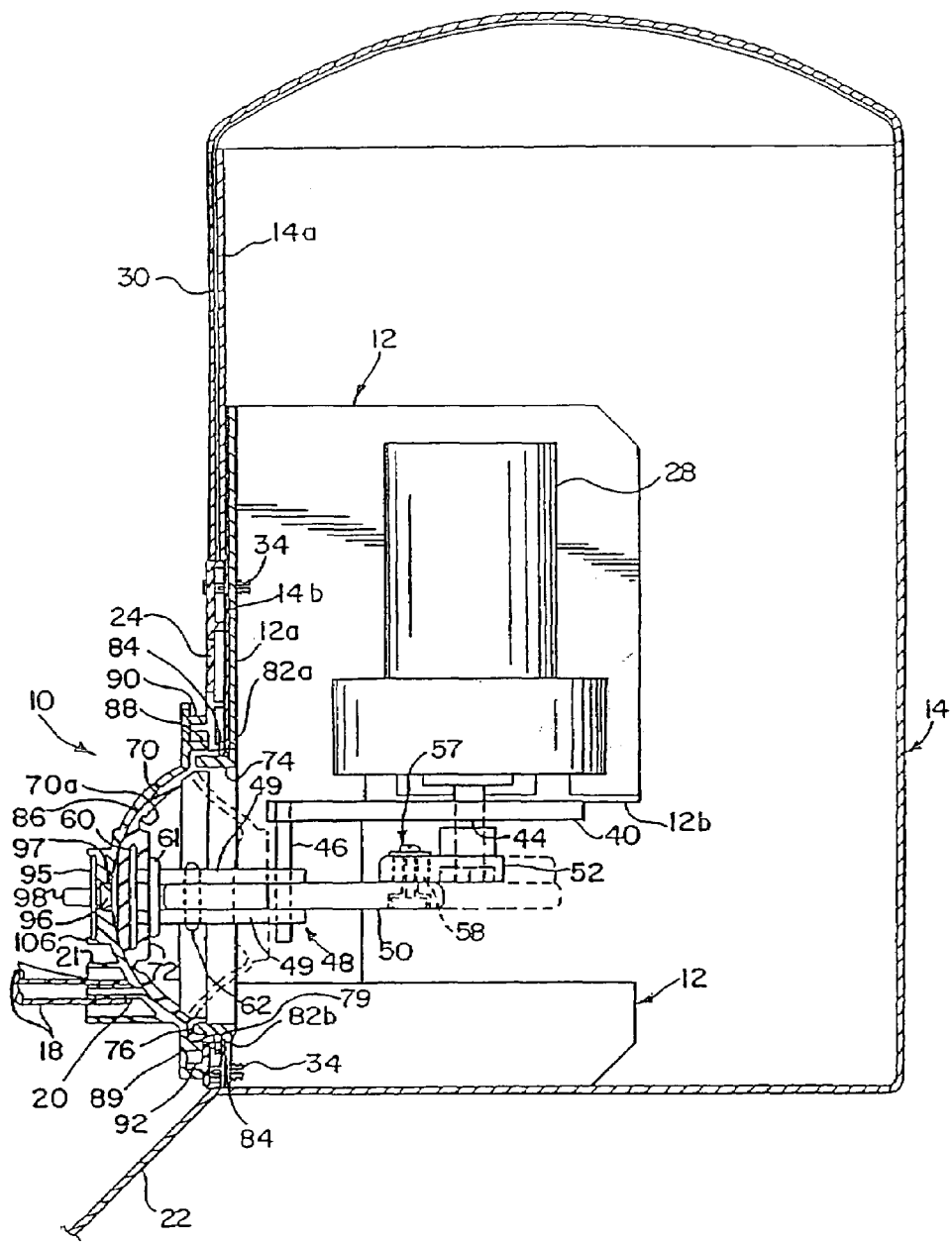
FIG. 2 is a cross-sectional view of the breastpump of FIG. 1 within a closed carrying case.

A cam or eccentric 52 is mounted on the drive shaft 44 (FIGS. 2 and 3). A collar-like portion 53 is formed off-center on the cam. The outboard end of the drive shaft 44 is received in a D-shaped opening 54 within the collar portion 53, with the drive shaft 44 keyed to the same shape in a snug fit. An e-clip or c-clip (not shown) can be attached to the end of the shaft to further secure the cam 52 on the shaft.

An aperture 56 is also formed off-center in the cam 52. When cam 52 is driven by the motor 28 turning the drive shaft 44, aperture 56 orbits around the drive shaft 44. Of course, and as will be evident from the further description below, the cam-and-drive shaft mechanism could be made to turn in less than 360° or reciprocate, and still achieve the desired movement.

Follower 50 (FIG. 3) is operably connected to the cam 52 via a hollow post 58 formed adjacent the rearward end of the follower 50. Post 58 has a diameter which is slightly smaller than that of the aperture 56 of the cam 52 within which it is received to freely rotate. For purposes of relative scale, the follower 50 shown herein has a longitudinal length of about 2.5 inches, and a lateral width of about 0.75 inch. A machine screw, washer and lock-nut combination 57 is additionally used for further, but movable fixation (FIG. 2). An alternative embodiment of follower 50 is shown in FIGS. 4 and 5.

On the forward end of the follower 50 is mounted the puller 48 (FIG. 3). Puller 48 has two parallel legs 49 which extend from a puller cap 59 (FIG. 9) formed of an end disk or button 60 and a disk-like flange 61 spaced slightly inboard from the end disk 60. Puller 48 is connected to the follower 50 via a spring pivot pin 62 (FIG. 3) which extends through and is fixed within holes 63 in the legs 49 (only one of which holes 63 is shown in FIG. 3), and extends through hole 64 in the follower 50. The follower 50 is thus captured between the legs 49, but can pivot on the pivot pin 62. A guide pin 46, which is fixed within holes 65a, 65b in the legs 49, extends through a crescent-shaped aperture 66 formed in follower 50 (FIG. 3). When the follower 50 is mounted to the cam 52, guide pin 46 extends into the slot 45 of the guide 40 (FIG. 2).

Figure 9:
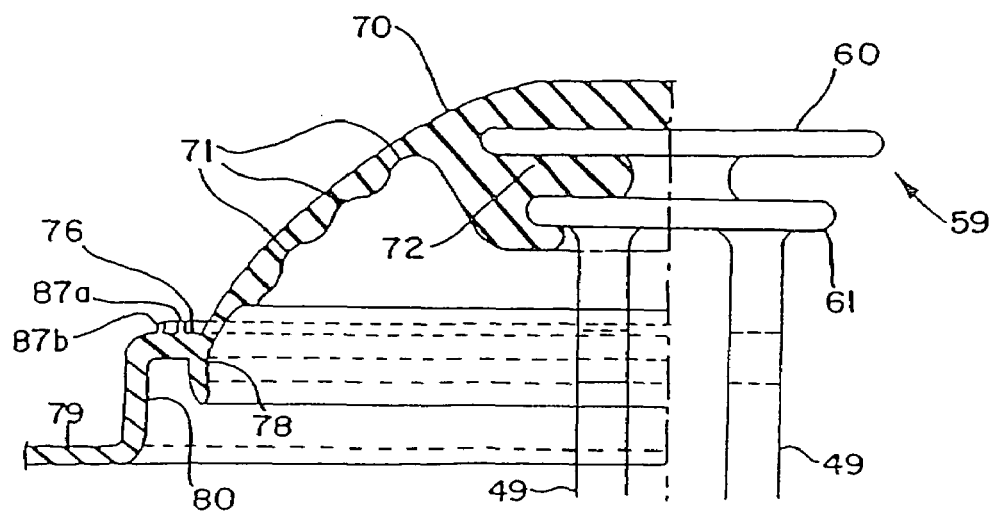
FIG. 9 is an enlarged partial view in section of an alternative form of the diaphragm.

A flexible diaphragm 70 is mounted on the end of the puller 48. Diaphragm 70 is preferably made of silicone, which could be rated for food contact but need not be, and has a general semi-spherical shape. End disk 60 (FIGS. 2 and 9) of the puller 48 is received within an orifice in the inboard side of the diaphragm 70, which orifice is formed by a thickened center part of the diaphragm 70 and a circular overlying flange part 72 (FIG. 2, and see detail of connection in FIG. 9). End disk 60 fits within this orifice in a button-like engagement. Flange disk 61 on the puller 48 presses against the flange part 72 of the diaphragm to further enhance the engagement. Alternatively, the diaphragm 70 could be molded integral with the end of the puller. It will be noted that a circumferential reduced wall thickness is formed in the diaphragm at 70a around the center area of the diaphragm 70 to facilitate flexion of the diaphragm. The wall thickness of the portion of the diaphragm 70 between the thickened center part and approximately the perimeter of the curved portion of the diaphragm is generally about 0.08 in.

An alternative form for the diaphragm wall is shown in FIG. 9. As shown in that figure, a corrugated or rippled interior provided by concentric channels 71 facilitate flexion of the diaphragm 70.

Figure 8:
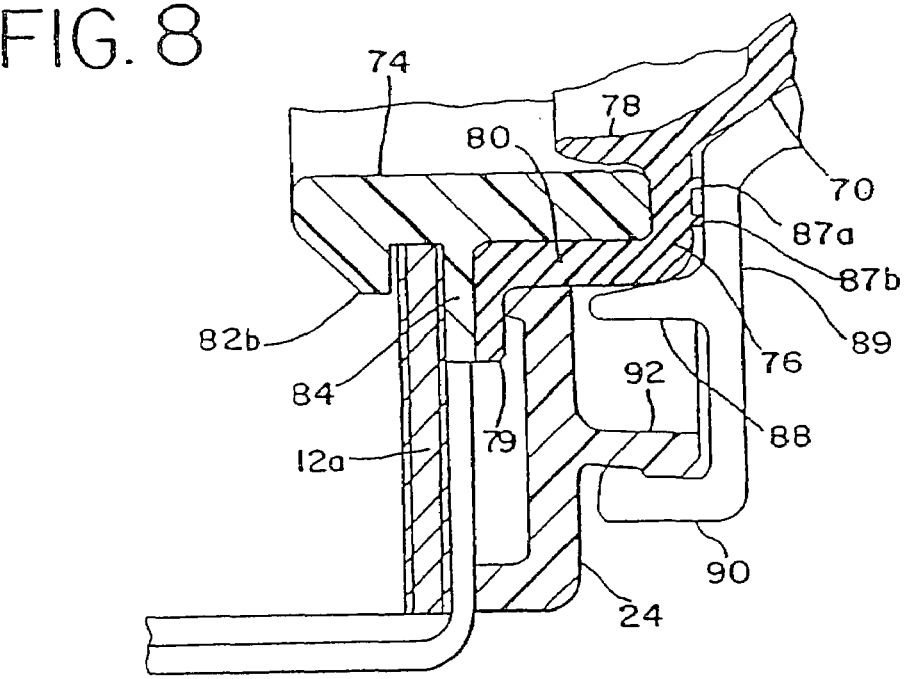
FIG. 8 is an enlarged partial view in section of the diaphragm pump mounting arrangement shown in FIG. 2.

As shown in FIGS. 2 and 8, diaphragm 70 is mounted to the front plate 24 using a diaphragm mounting ring 74. Diaphragm 70 has a perimetrical shoulder 76 formed thereon from which depend inner and outer concentric circular flanges 78 and 80, respectively. With shoulder 76, flanges 78 and 80 form a circular channel. The outboard part of mounting ring 74 is received within this channel in a slip-on type fit of the diaphragm.

With the diaphragm 70 so mounted thereon, mounting ring 74 is received in an aperture formed in the front plate 24 and the frame front 12a. Two locking tabs 82a, 82b (FIGS. 2 and 8) extend outwardly at opposite sides of the mounting ring, and engage within cut-outs formed in the aperture of the frame front 12a to position the mounting ring by rotating the mounting ring into place.

A thin-width radial ring 84 (FIG. 8) is formed around the outside circumference of the mounting ring 74. This ring 84 underlies an outwardly extending lip 79 provided on the diaphragm 70, which lip 79 is pressed between the front plate 24 and the ring 84.

Overlying the diaphragm 70 (FIG. 8) is a rigid housing cap 86 (FIG. 2) made of polypropylene. Cap 86 has an inner surface roughly matching the curvature of the diaphragm 70, such that the diaphragm rests close to or against the interior surface of the cap 86. The cap 86 has a ring-like portion 89 extending outwardly from the edge of the semi-spherical dome portion of the cap 86. Concentric inner and outer cap flanges 88 and 90, respectively, depend from the ring-like portion 89 (see FIGS. 7 and 8 in particular). Inner cap flange 88 presses against the outboard side of outer diaphragm flange 80, with part of ring-like portion 89 overlying diaphragm shoulder 76. In conjunction with the mounting ring 74, this forms an air seal between the cap 86 and the underlying diaphragm 70. Additional concentric ribs 87a, 87b (FIGS. 8 and 9) are formed on top of the diaphragm shoulder 76 out of the same material as the diaphragm, and serve to facilitate this seal through compression against the cap shoulder 89. Outer flange 90 of the cap 86 is received in a snap-engagement with a cap mounting ring or collar 92 formed on the face of the front plate 24 to mount the cap 86 in place.

It will be recognized that the diaphragm 70 is one element that is moved relative to another member or base (the cap 86) to form an expansible chamber that has an expanding and contracting volume. Other such expansible chambers are considered to be adaptable to aspects of this invention, although the flexible diaphragm and cap arrangement has proved most advantageous at this time.

In operation of the pump 10, motor 28 is actuated, as by a standard on-off circuit utilizing switch 94 mounted in the front plate 24. Drive shaft 44 rotates cam 52 causing follower 50 to move rearwardly (relative to the front plate 24) and then forwardly. Puller 48 in turn moves rearwardly with the follower 50, drawing diaphragm 70 away from the inside of the cap 86. This generates a negative pressure (vacuum) in the space thus formed between diaphragm 70 and cap 86 (see dotted-line position of the drive chain elements and diaphragm in FIG. 2).

The rotation of the cam 52 with its movement of the pivotable follower 50 is designed to generally generate and follow the type of vacuum curve, and cycles per minute, shown and described in Medela U.S. Pat. No. 5,007,899. Guide 40 serves to constrain the pivoting movement between the puller 48 and follower 50.

The negative pressure generated within the cap 86 is communicated through the outlet provided by the spigots 20 to one or both of the tubes 18 (depending on whether one or two breast shield assemblies 16 are being used). If only one breast shield assembly 16 is being used, it is contemplated that a cap 102 (FIG. 10) would be used to close the spigot 20 not being used. The cap 102 would further include a small vent hole 103 designed to nonetheless admit some air through the spigot and thereby into the cap interior in a manner to normalize the vacuum between single and double pumping usage, i.e., so that the vacuum drawn in a shield is about the same when only using one breast shield as when both breast shield assemblies are attached. Cap 102 has a loop end 104 to tether the cap 102 to one of the spigots 20.

A vacuum regulator is additionally provided for adjustment of the level of vacuum from the pump. This regulator takes the form of a flap-type valve disk 95 (FIG. 7) mounted in a circular-shaped depression formed in the center of hemispherical diaphragm cap 86. Valve disk 95 has a knob 96 (FIG. 2) which is received in a lipped aperture 97 formed in the foregoing depression, in a pop-in fit. A knurled stem 98 extends from the valve disk 95 which is grasped to rotate the valve.

When valve disk 95 is rotated, a hole 100 through the disk 95 can be aligned with one or the other of holes 99a, 99b (FIG. 7) extending through the depression into the interior of the cap dome, or placed out of alignment with either hole 99a, 99b, the latter both then being covered and closed by the valve disk 95. Holes 99a and 99b are of different diameters, such that more air will pass through one than the other when aligned with disk hole 100. Accordingly, a preset "medium" (smaller diameter hole), "minimum" (larger diameter hole) or "maximum" (both holes covered) vacuum level range is provided. Crescent-shaped aperture 101 formed through the cap 86, which is under the disk valve 95, serves to vent air admitted into the cap interior (within the diaphragm/cap space created by the vacuum stroke) on the forward or compression stroke of the diaphragm 70 (diaphragm 70 moving toward the cap interior).

FIG. 7A shows a modified form of a vacuum regulator similar in concept to that of FIG. 7. In this form, hole 100 is formed through the disk 95, but extends into a crescent-shaped channel 105 formed in the underside of the valve disk, i.e., the part in facial engagement with the cap 86. As in the previous version, the disk 95 is located in a short well 106 defined by a collar (see FIG. 2). Disk 95 is rotated so that the channel 105 can be put in communication with one hole 99a, both hole 99a and 99b, or neither hole, for medium, minimum and maximum pressure, respectively. Also, a vent or leakage groove 107 is provided in the well beneath the disk 95 from a hole 99a and extending into and upwardly out of the collar 106. This provides a desirable amount of constant air leakage into the cap even at maximum negative pressure. This air leakage assures that there will be some air within the cap to apply a positive pressure on the return stroke, which can be used as a pneumatic assistant to move milk from a catch chamber into the container.

Yet another form of vacuum regulation device is shown in FIGS. 7B through 7E. In this embodiment, a rotatable regulator disk valve 200 fits upon a rim or collar 201 formed on the rigid cap 86". A channel or recess 202 is formed on the outside of the rim 201. The channel is of constant width but of increasing depth (going from bottom to top as viewed in FIG. 7C). A port or hole 203 is in the deepest part of the tapered channel 202, and extends through the cap 86".

Disk valve 200, which can be made of a somewhat flexible rubber material, has a nub 204 that fits within an appropriately sized aperture formed in the rim/cap, with a collar 204a that catches against a sidewall edge defining the aperture to rotatably mount the disk valve 200 in place. On the inside of the disk valve sidewall 200a is a recess 206 which communicates with atmosphere.

Thus, with the disk valve 200 turned so that its recess 206 is located over the shallowest part of the rim channel 202 and furthest from the hole 203, air "leakage" into the cap 86" interior-through the disk valve recess 206 into the rim channel 202 and through the hole 203—is at a minimum. As the disk valve 200 is rotated so that its recess 206 is located at a deeper part of the channel 202, air flows more freely to the hole 203 and into the cap interior, toward a maximum when the recess 206 is over the deepest part of the channel 202 adjacent hole 203. A continuously variable vacuum regulating device is thereby provided.

A diaphragm pump is thus provided which is of relatively small size, with a durable drive chain. In the disclosed environment of a breastpump, it fits handily within a soft carrying case for quick and easy hook-up to one or more breast shield assemblies, which can be carried in the case.

It is envisioned that a thin disposable membrane-like cover (not shown) may additionally be provided over the diaphragm 70. This disposable cover would be between the diaphragm 70 and inside of the cap 86, and serve to further hygienically isolate the diaphragm 70 from any milk, air or the like which could be pulled within the cap 86 in the vacuum stroke. This disposable cover would be particularly useful if there were multiple users of the pump 10. Cap 86 would simply be removed and sterilized, and the disposable cover replaced between users. Alternatively, a separate cap 86, which itself might be disposable, for each user with a disposable cover could be provided.

Figure 12:
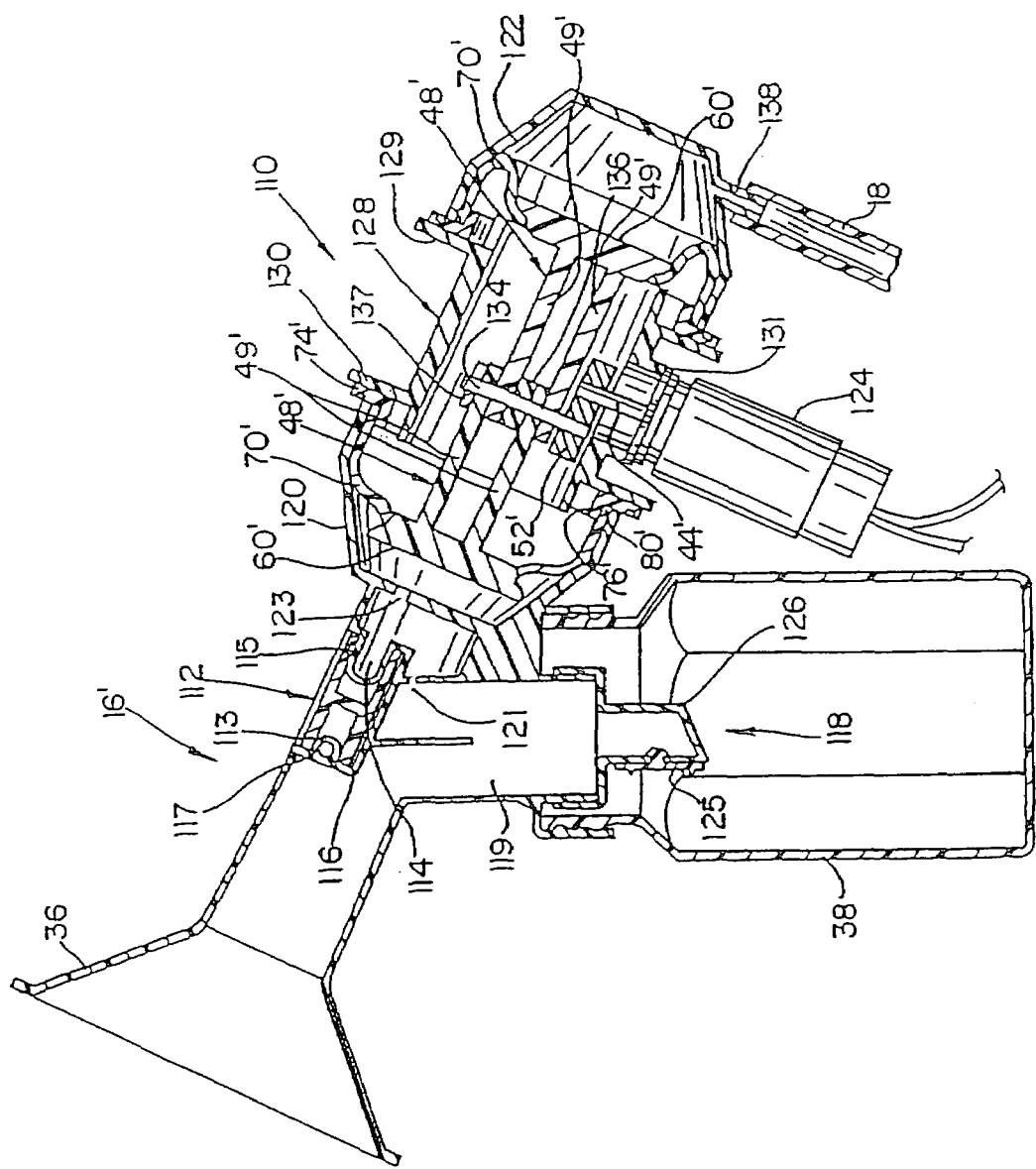
FIG. 12 is an enlarged sectional view of the breastpump of FIG. 11 having the pumping units attached thereto.
Figure 13:
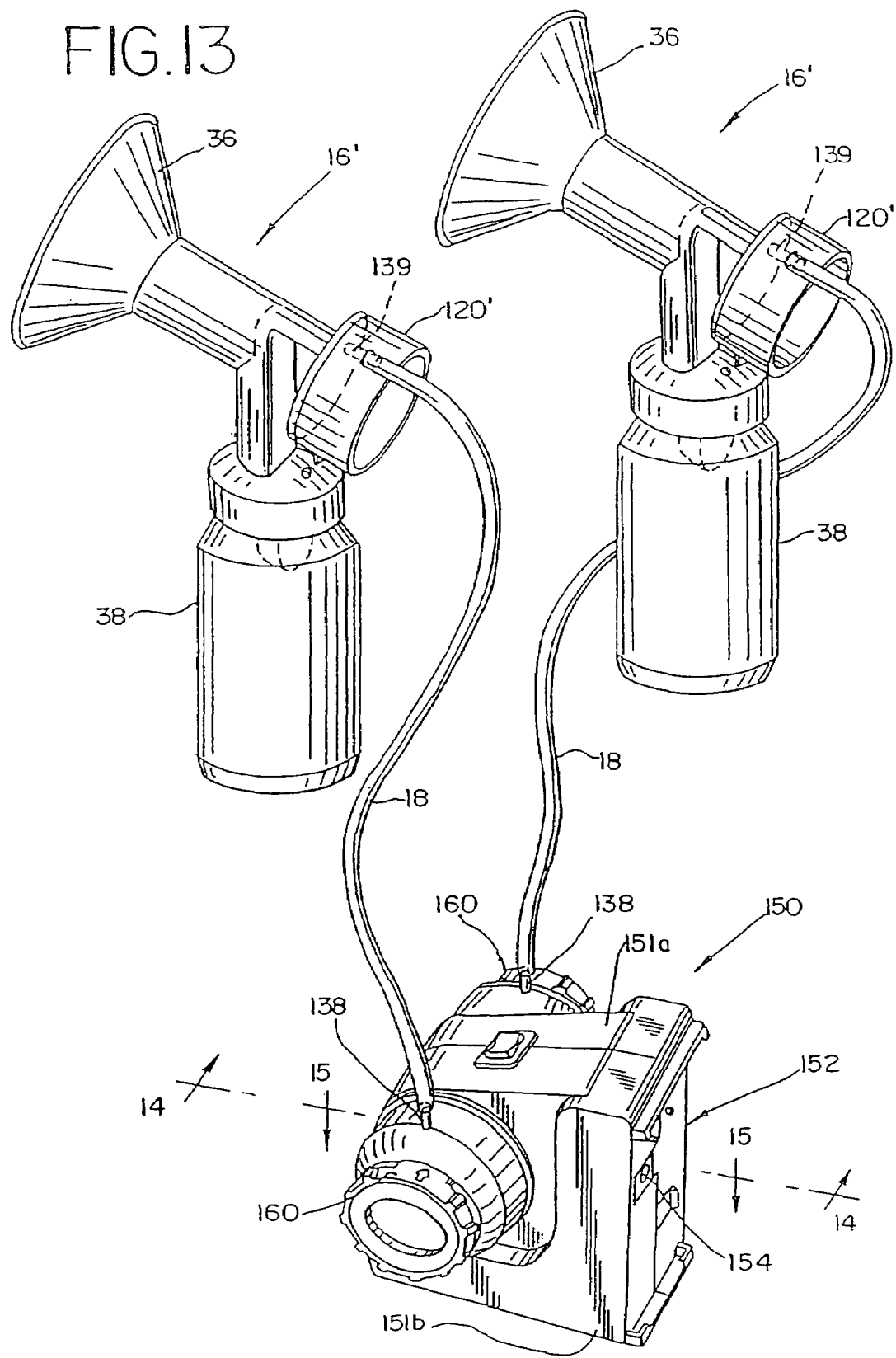
FIG. 13 is yet another embodiment of the invention taking the form of a tabletop version.
Figure 14:
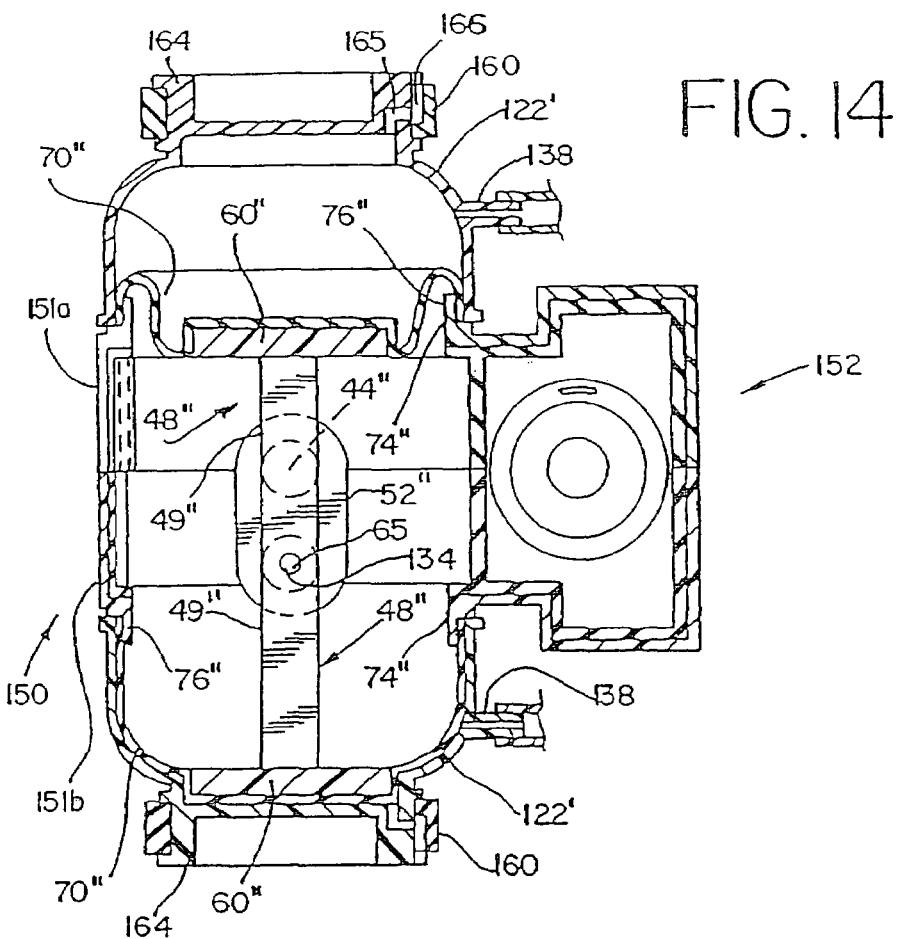
FIG. 14 is a sectional view taken along line 14-14 of FIG. 13.
Figure 15:
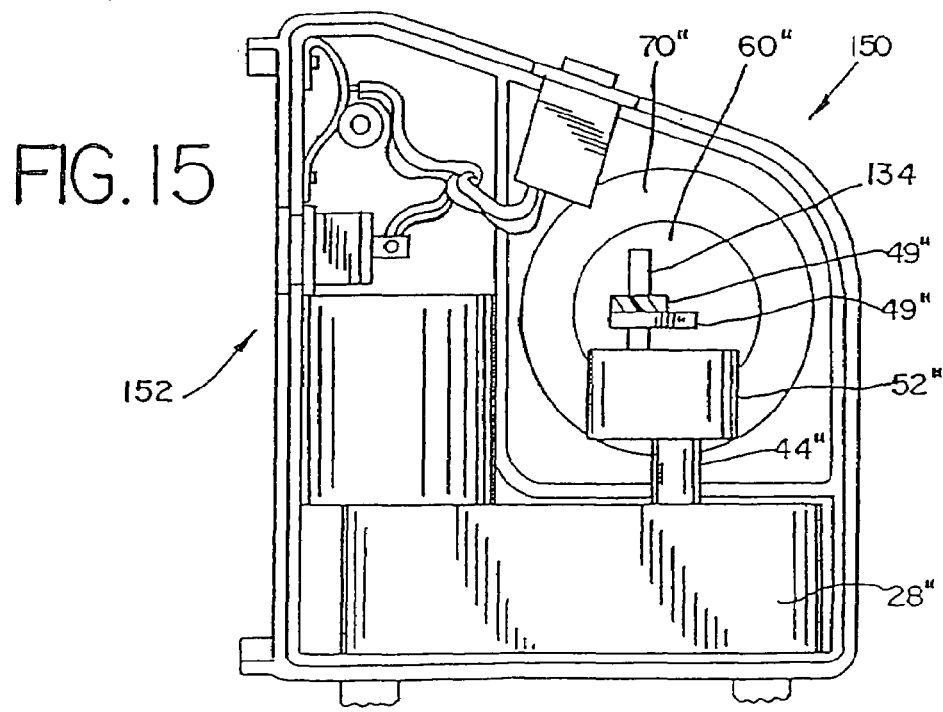
FIG. 15 is a sectional view taken along line 15-15 of FIG. 13.
Figure 16:
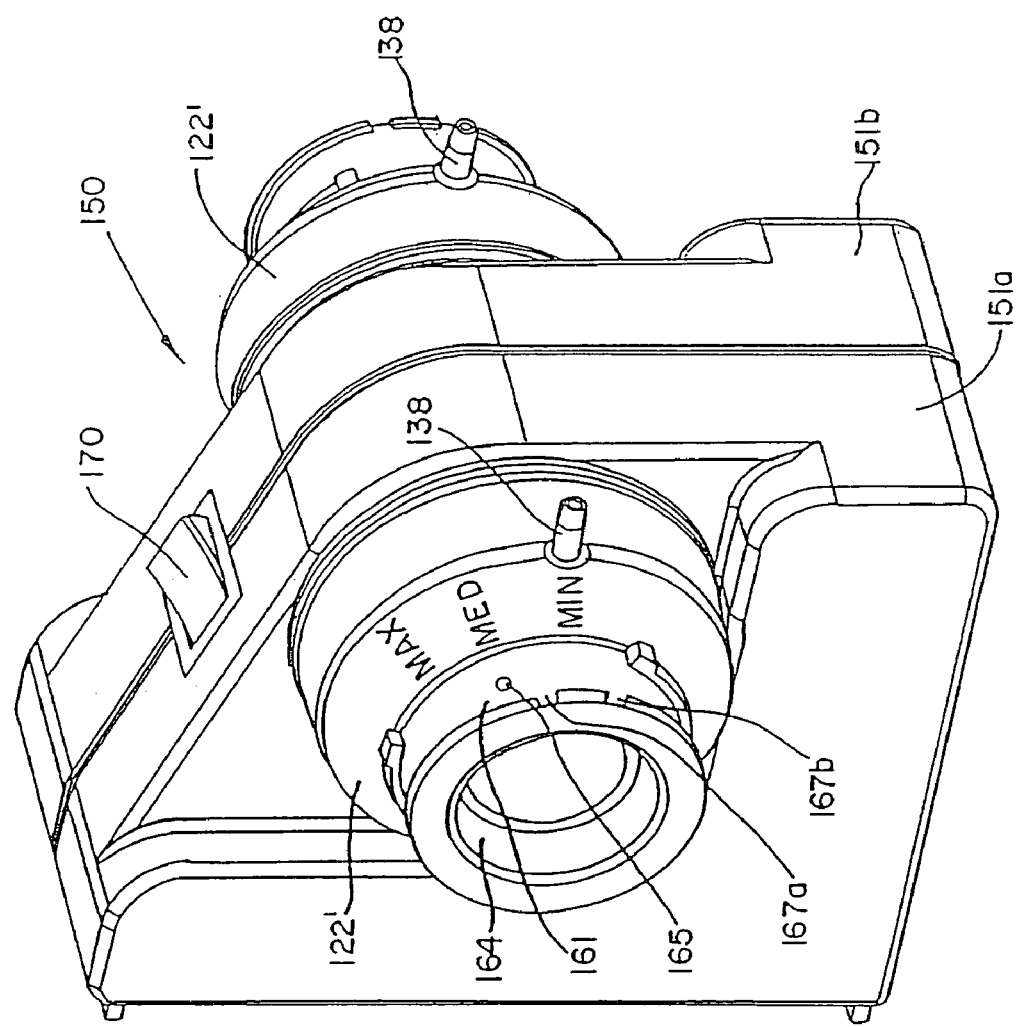
FIG. 16 is an enlarged view of the pump of FIG. 13, with the vacuum adjusting ring removed.

Turning now to FIGS. 11 and 12, another embodiment of the invention takes the form of a double-diaphragm pump, i.e., a pump that has two diaphragms, which is particularly adapted for double-pumping (although, as will be seen, it also has a single-pumping mode of operation). The double pump is generally shown at 110. It communicates vacuum (as will be described below) to breast shield assemblies 16' (again, prime numbers indicate generally similar elements to their unprimed counterparts). Breast shield assemblies 16' include a vacuum regulator 112 which modifies the amount of reduced pressure generated by the pumping action. The regulator 112 comprises a rotary member 113 with an internal groove or passage 115. The rotary member 113 has hollow ends. One hollow end encircles a ported structure 114 in the form of a nub having a pair of holes or ports (not shown). The rotary member 113 fits within a cavity 116 formed in the breast shield assembly 16'. The ported nub 114 is at one end of the cavity, and a boss 117 is at the other end. The other hollow end of rotary member 113 is received on the boss 117 to rotate thereon. Reduced pressure is adjusted by positioning the internal groove 115 of the rotary member 113 over one, both or neither of ports of the ported nub 114. The internal groove 115 is open to atmosphere. The ports extend into the interior of the breast shield assembly 16'. Depending upon whether the internal groove 115 is over one port or both ports, suction or reduced pressure is thereby modified by allowing air to bleed into the breast shield assembly 16' through the vacuum regulator 112. The regulator 112 is easily rotated, and conveniently located, allowing the user to manipulate it with one finger, if desired.

A valve mechanism 118 is located at the lower portion of catch chamber 119. The valve mechanism 118 is described in U.S. Pat. No. 4,929,229, with a flexible disk 125 mounted to cover openings in a valve housing 126 in a flap-valve fashion. When the breast pump is operated, the disk 125 is caused to close underlying apertures in the valve housing 126 under negative pressure, thus closing the collection chamber 119. When the vacuum is released, milk collected in the collection chamber 119 flows downwardly into the container 38 through the apertures past the disk 125. The valve housing 126 may be attached to the outside of a short tubular extension of the collection chamber 119 via a snug interference fit.

The double-diaphragm pump 110 is adapted to be carried by one of the breast shield assemblies 16', enhancing its portability. To this end, one or (as shown here) both of the assemblies 16' has an enlarged collar or skirt 120 formed thereon, which is in communication with the shield 36 via orifice 121. This collar 120 forms a generally hemispherical rigid shell much like that of rigid cap 86 of the embodiment described in regard to FIG. 2, for example, and functioning to the same end. A rigid cap 122 is also provided for the double-diaphragm breast pump 110, which again is similar to that of the rigid cap 86 in function, as discussed hereafter.

As shown in FIG. 12, the double-diaphragm pump 110 has a motor 124, which in this embodiment is a suitable DC gear motor. Motor 124 is fixedly mounted to a pump housing 128. Pump housing 128 is generally cylindrical (tubular), with radially extending disk-shaped mounting flanges just inboard from each end. The motor 124 extends through and is held within a motor mount 131 formed by a hole extending through the side of the housing body 128. A motor cover (not shown) would preferably surround the motor 124.

A drive shaft 44' extends from the motor 124 and is rotated by the motor. Fixed to the drive shaft 44' is an eccentric element 52'. Fixed to and extending from the eccentric 52' is a pin 134, which functions much like the post 58 of the aforedescribed embodiment of FIG. 2. That is, as eccentric 52' is rotated by the drive shaft 44', the pin 134 will orbit the drive shaft.

Mounted upon the pin 134 are a pair of pullers 48'. Each puller 48' has a pair of parallel legs 49'. Holes 65*a*, 65*b* are provided in each of the legs through which the pin 134 is received. The pin 134 rotates freely within the holes 65*a*, 65*b*. It will be noted that the pullers 48' extend in opposite directions, with the legs 49' of the pullers staggered when mounted on the pin 134. A spacer 136 is used between two legs of the respective pullers 48'. A retaining nut 134 is mounted on the free end of the pin 134 to retain the pullers 48' in place.

In this embodiment, a flexible diaphragm 70' is fixed in place, as by insert molding, silicone glue or the like, to an end disk 60' of each puller 48'. One of the diaphragms 70' is received within the hemispherical shell formed by collar 120. This is accomplished using a diaphragm mounting ring 74' having an upstanding collar or shoulder 76'. Lip 80' of the diaphragm 70' (FIG. 12) fits over the outboard side of the shoulder 76' in an airtight engagement. When this diaphragm 70' is inserted within the collar 120, its flange 80' is pressed between the inboard side of the collar 120 and the outboard side of the shoulder 76', in essence forming a gasket. This seals its engagement with the collar 120, and retains the pump 110 within the breast shield assembly 16'. An identical mounting arrangement is used for the other diaphragm 70' within the rigid cap 122.

Of course, the mounting arrangement for the diaphragm 70' could also be adapted in a manner as shown in FIG. 8. The diaphragm could also be glued to the ring 74'.

In operation of the embodiment of FIGS. 11 and 12, one of the diaphragms 70' of the double-diaphragm pump 110 is mounted within the collar 120 of a breast shield assembly 16'. A rigid cap 122 is placed over the other diaphragm 70'. When the motor 124 is actuated, each of the diaphragms 70' is caused to reciprocate, thereby generating an intermittent vacuum (negative pressure) in its respective breast shield 36. This vacuum will obviously alternate between the breasts. Reciprocation is accomplished through the action of the pin 134 as it revolves with the eccentric 52', pulling one puller 48' and pushing the other.

With respect to the vacuum being generated within the rigid cap 122, it is communicated to the remote breast shield assembly 16' via tubing 18. One end of the tubing 18 is connected to a spigot 138 formed with the cap 122, and a spigot-like adapter 139 inserted into the other tube end and into an aperture formed in the collar 120. Of course, if only one breast is to be pumped at a time, the tubing 18 need not be connected, and the cap 122 can simply be vented to atmosphere.

Yet another double-diaphragm embodiment is shown in FIGS. 13 through 17. This takes the form of a table-top version, generally indicated at 150. In this embodiment the double-diaphragm pump is located within a two-piece rigid housing having housing halves 151*a* and 151*b*. Formed integral with each housing half is a diaphragm mounting ring 74" (FIG. 14) with upstanding collar or shoulder 76". Received thereon is a respective diaphragm 70". The diaphragms 70" can most preferably be integrally molded with the housing halves. A hemispherical rigid cap 122' is provided for each housing half, and serves to form an airtight engagement with the diaphragm 70" in the same manner as described with respect to the other double-diaphragm embodiment. A spigot 138 extends from each of the caps 122', and is connected to a respective breast pump assembly 16' via tubing 18 in the manner previously described. It will be noted that the collar 120' shown in this embodiment is not exactly the same as collar 120, in that it is not specifically adapted to receive a diaphragm of the type described with regard to FIGS. 11 and 12, although it could be made so, if desired. Herein, collar 120' is meant to represent that on a conventional breast pump assembly that could receive a manually driven piston pump, such as shown in U.S. Pat. No. 4,929,229.

Referring again to FIGS. 14 and 15, this table-top double-diaphragm pump utilizes pullers 48" having a single leg 49'''. A single hole 65 is provided in the inboard side of each leg 49", within which pin 134 is rotatably received. Pin 134 is fixed to an eccentric 52", which in turn is fixedly mounted to a drive shaft 44" rotated by motor 28". In this embodiment, motor 28" is again a DC gear motor. Motor 28" is capable of being driven by a standard rechargeable battery (not shown), such as a NiCd or NiMH camcorder-type battery, which would be mounted in place on the housing in standard well known fashion, as at battery mounting sidewall 152. An alternative DC adapter for use with an AC power source can be provided (not shown), which would be electrically connected at port 154, again using standard circuitry and adapter technology which is well known.

Each puller 48 has an end disk 60 which is fixed to a diaphragm 70", as by welding, gluing or the like. The pullers 48" are reciprocated in the same manner as previously described under action of the pin 134 orbiting on the eccentric 52". Vacuum is alternatingly generated in the respective breast shield assemblies 16' in this manner.

In this table-top embodiment 150, the caps 122' are each provided with a vacuum regulation device. This takes the form of a flexible ring 160 which is mounted in a channel 161 (FIG. 16) formed in a collar portion 164 that extends outwardly from the cap 122'. Flexible ring 160 overlies a vent hole 165 which communicates with the space between the interior of the cap 122' and the diaphragm 70". The flexible ring 160 forms an air seal with the channel 161, except for a portion 166 comprising a small channel 166 in the ring 160. This small channel 166 is rotatable to positions where it will connect one, both or none of apertures 167a, 167b formed in the radially extending outboard lip 164a of the collar portion 164. This respectively will correspond to a previously determined medium (one aperture), minimum (both) or maximum (neither) vacuum pressure. This pressure regulation is advantageously independently provided for each breast shield in this manner.

Motor 28" is actuated by on-off rocker switch 170. It is contemplated, however, that the motor drive could be modified to include an adjustable speed regulation, such as through use of a circuit having an adjustable diode arrangement for current control to the motor.

The embodiment of FIGS. 13 through 18 also provides a sound-deadening and vibration-reducing feature. This is provided by soft material such as Santoprene supplied by Advanced Elastomer Systems, of Akron, Ohio. This is a thermoplastic elastomer which is insert-molded into each housing half 151a, 151b. As shown here, this material is formed in a pyramidal pattern 175 on the broadest part of interior sidewalls of each half 151a, 151b, and in an elongated peak-and-valley pattern 176 along the remainder of each half. Other patterns could be used.

Feet 176 (FIG. 17) are also molded on the housing valves 151a, 151b using the same thermoplastic elastomer.

Most desirably, the sound/vibration reducing material, feet 176 and diaphragms 70", are all insert-molded at the same time with the housing valves. This greatly reduces and simplifies assembly.

FIGS. 19 and 20 show designs which would be variants on the type of diaphragm pump shown in the embodiment of FIGS. 11 and 12. These variants would be single pump versions, i.e., not specifically adapted for double-pumping. The FIG. 19 embodiment, for instance, would have a housing 180 for the elements described with the FIGS. 11 and 12 version, except only a single diaphragm pump would be provided. An on-off switch is shown at 181, and mounting collar at 120'. The FIG. 20 embodiment would likewise include the elements of the FIG. 19 embodiment, but is shown in an alternative mounting arrangement, with the diaphragm pump mounting collar 120" extending from the top of the breast shield assembly.

In still another variation on a pump for double breast pumping, the embodiment of FIG. 21 is particularly adapted for pumping both breasts simultaneously, i.e., negative pressure is transmitted to both breasts at the same time. In this proposed version, the motor 28''' has an output shaft 44''' on which an eccentric or cam 52''' is mounted for rotation as in previous described embodiments. A puller 48''' is likewise similarly mounted to the eccentric 52'''. A guide 40" is again used to facilitate movement of the diaphragms 70''', two of which are employed. Guide 40" has a channel 45" into which the motor shaft 44''' is received. An end of the guide 40" is fixed to a yoke 190. An end of puller 48''' is likewise fixed to the yoke 190 with a swivel joint connection 191.

The two diaphragms 70''' pass through a sheet metal frame 192. The yoke 190 has openings 193 which receive and hold end elements 194 of the diaphragms 70'''. The diaphragms 70''' are themselves mounted within orifice 194 formed in a mounting plate 195. Overlying each of the diaphragms 70''' and fixed, as by screws (not shown), to the mounting plate 195 are plates 24' having rigid caps 86' from which extend spigots 20'. Diaphragms 70''' operate in conjunction with the caps 86' in the manner previously described. The entire pumping mechanism can be mounted within a bag 14', again as in a manner previously described (i.e., FIG. 1).

In operation of the FIG. 21 embodiment, rotation of eccentric 52''' causes the puller 48''' to orbit the drive shaft 44'''. This action in turn causes the yoke 190 to move toward and then away from the frame 192, to thereby reciprocate the diaphragms 70''', simultaneously generating a negative pressure in the respective expansible chamber formed by a diaphragm 70''' and its rigid cap 86'. That negative pressure is communicated through a spigot 20' to a breast shield assembly via tubing, as previously described.

While the invention has been described with respect to a number of embodiments, those with skill in the art will recognize other materials, arrangements, modifications and the like which can be advantageously utilized, yet which will still fall within the scope of the inventive concept, and the claims set forth hereinafter.

What is claimed is:

1. A pump mechanism for a breastpump, comprising:
   a motor-driven drive train including a crank connected to a pair of suction subassemblies, each suction subassembly further having a connecting rod rotatably connected to the crank at a first end, a diaphragm connected to the connecting rod at a second end, a base member sealably connectable to the diaphragm to cooperatively define a expansible chamber therebetween, the base member being constructed and arranged to produce at least a negative pressure upon movement of the diaphragm and having an outlet in communication with the expansible chamber and a breastshield, whereby a change in pressure produced in the expansible chamber is communicated to the breastshield.

2. The pump mechanism of claim 1, wherein each connecting rod second end includes a piston portion.

3. The pump mechanism of claim 2, wherein each piston portion is connected to a respective diaphragm.

4. The pump mechanism of claim 1, wherein the crank includes at least one eccentric portion.

5. The pump mechanism of claim 4, wherein each eccentric portion functions as a cam.

6. The pump mechanism of claim 1, wherein each suction subassembly expansible chamber communicates with a respective breast shield.

7. The pump mechanism of claim 1, further comprising a housing, in which the motor-driven drive train is disposed.

8. The pump mechanism of claim 7, wherein the diaphragms are disposed on opposite sides of the housing.

9. The pump mechanism of claim 8, wherein the base members are disposed on a side of the diaphragms opposite the housing.

10. The pump mechanism of claim 9, wherein the pair of base members are each a rigid cap.

11. The pump mechanism of claim 1, wherein the motor-driven drive train is arranged to produce a negative pressure in both of the pair of subassemblies simultaneously.

12. A pump mechanism for a breastpump comprising:
a motor;
a first and a second expansible chamber, each expansible chamber having an element which is moveable relative to a base member with the element and base member being generally air sealed with respect to each other so as to form a variable volume therebetween and produce at least a negative pressure by movement of the element relative to the base member,
an outlet provided in communication with each expansible chamber for connecting to a breastshield in communication with a respective variable volume and;
a drive train connected to the motor to move each expansive chamber element relative to a respective base member, wherein the element is a flexible diaphragm and the base member is a rigid member to which the diaphragm is mounted and having a respective outlet formed in the rigid member, the diaphragm being movable in relation to the rigid member by the drive train, which includes an eccentric rotated by the motor, with a pair of pistons mounted to move with the eccentric, the diaphragms of the first and second expansible chambers being connected to the pistons, so as to expand and contract the volumes of the expansible chambers as the eccentric is rotated.

13. A pump mechanism for a breastpump comprising:
a motor;
a drive train connected to the motor, the drive train including a crank and a pair of connecting rods rotatably connected to the crank;
a pair of diaphragms, with each of the pair of diaphragms connected to a respective one of the pair of connecting rods;
a pair of base members defining at least in part a respective first and a second expansible chamber, each expansible chamber being generally air sealed with a respective one of the pair of base members so as to form a variable volume therein and produce at least a negative pressure by movement of the diaphragms relative to a the base members, and
an outlet provided in communication with each of the first and second expansible chambers for connecting to a breastshield in communication with a respective the variable volume.

14. The pump mechanism of claim 13, wherein each of the pair of connecting rods includes a piston portion, each the piston portion of the connecting rods being connected to one of the pair of diaphragms.

15. The pump mechanism of claim 13, wherein the crank includes one or more eccentric portion.

16. The pump mechanism of claim 15, wherein the eccentric portion functions as a cam.

17. The pump mechanism of claim 15, wherein the crank includes a pin attached to the one or more eccentric portion.

18. The pump mechanism of claim 17, wherein the pin is attached normal to the eccentric portion.

19. The pump mechanism of claim 13, further comprising a housing, in which the drive train is positioned.

20. The pump mechanism of claim 13, wherein the housing is a one-piece, generally cylindrical housing.

21. The pump mechanism of claim 20, wherein the pair of diaphragms is disposed on opposing ends of the housing.

22. The pump mechanism of claim 20, wherein the base members are disposed on opposite sides of the housing.

23. The pump mechanism of claim 22, wherein the pair of base members are each a rigid cap.

24. A pump mechanism for a breastpump comprising:
a motor;
a crank connected to the motor;
a pair of connecting rods rotatably connected to the crank;
a pair of diaphragms, each of the pair of diaphragms connected to a respective one of the pair of connecting rods;
a pair of caps, each of the rigid caps defining with a respective one of the pair of diaphragms a respective first and a second expansible chamber so as to form a variable volume therein and produce at least a negative pressure by movement of the diaphragms relative to a the caps, and
an outlet provided in each of the pair of caps in communication with the first and second expansible chambers for connecting to a respective breastshield in communication with a respective the variable volume.

25. An improved pump mechanism for a breastpump capable of double-breast pumping using two beat shields where the improvement comprises:
a motor;
a drive train connected to the motor; and
a pair of diaphragm pumping chambers, connected to the drive train and adapted to produce a negative pressure by movement of a diaphragm in its respective chamber, with an outlet provided in each of the pair for connecting to a respective breastshield.

* * * * *